(12) United States Patent
Wright

(10) Patent No.: US 9,126,902 B1
(45) Date of Patent: Sep. 8, 2015

(54) PREPARATION AND THERMAL CURING OF SINGLE-RING BIS(CYANATE) ESTER MONOMERS

(71) Applicant: The United States of America, as represented by the Secretary of the Navy, Washington, DC (US)

(72) Inventor: Michael E. Wright, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 154 days.

(21) Appl. No.: 13/681,226

(22) Filed: Nov. 19, 2012

Related U.S. Application Data

(63) Continuation-in-part of application No. 13/678,864, filed on Nov. 16, 2012.

(60) Provisional application No. 61/562,242, filed on Nov. 21, 2011, provisional application No. 61/562,118, filed on Nov. 21, 2011.

(51) Int. Cl.
*C07C 263/00* (2006.01)

(52) U.S. Cl.
CPC .................... *C07C 263/00* (2013.01)

(58) Field of Classification Search
None
See application file for complete search history.

(56) References Cited

PUBLICATIONS

Database Caplus Chemical Abstracts Service, Columbus, Ohio, US; Database Accession No. 1973:536751, Abstract of Kurth et al. Chemische Berichte (1973), 106(8), 2419-26.*
Hamerton et al., Polymer 42 (2001) 2307-2319.*
Synthesis of 3,5-dihydroxybenzoic acid (γ-resorcylic acid) from benzoic acid see: Suter, C. M.; Weston, A. W. J. Am. Chem. Soc. 1939, 61, 232.
γ-resorcylic acid esters were prepared by modifying the procedure of Suter, C. M.; Weston, A. W. J. Am. Chem. Soc. 1939, 61, 531.
Chemistry and Technology of Cyanate Esters, Hamerton, I. Ed.; Chapman and Hall: Glassgow, 1994.
Barton, J.M.; Chaplin, A.; Howlin, B.J.; Shaw, S.J. Polymer 2001, 42, 2307-2319.
PG alkylation in 20% yield: Steidl et al.. J. Mater. Chem. 2009, 19.

* cited by examiner

*Primary Examiner* — Karl J Puttlitz
(74) *Attorney, Agent, or Firm* — Charlene A. Haley

(57) ABSTRACT

A class of modified single-ring cyanate esters which have shown the ability to tailor and control the glass-transition (Tg) of the cured resins as well as the water uptake.

9 Claims, 5 Drawing Sheets

PREPARATION AND THERMAL CURING OF SINGLE-RING BIS(CYANATE) ESTER MONOMERS

CROSS-REFERENCE TO RELATED APPLICATIONS

This is a non-provisional patent application, claiming the benefit of, parent application Ser. No. 61/562,242 filed on Nov. 21, 2011, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to a class of modified single-ring cyanate esters which have shown the ability to tailor and control the glass-transition (Tg) of the cured resins as well as the water uptake.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to a class of modified single-ring cyanate esters which have shown the ability to tailor and control the glass-transition (Tg) of the cured resins as well as the water uptake.

No examples exist for making high performance composite resins from renewable resources (i.e. bioaromatics) in an efficient and cost effective manner. Phloroglucinol is a viable and cost effective source of bioaromatics (DRATHS corp. markets a bio-version). This work also solves the problem of water uptake in cyanate ester resins by tailoring the structure of the monomer in a systematic and unprecedented manner. See attached disclosures included in this application.

The NAVY often works in wet humid environments. The NAVY and DoD also are accelerating weapons faster and flying them faster (i.e. hypersonics/kinetic weapons). The need for new high performance (HP) composite resins that do not suffer from "water issues" will provide a distinctive advantage to NAVY weapon platforms. This work is particularly important for the NAVY since it addresses and solves the problem of performance knock downs due to moisture uptake in composite materials and provides a tougher better high performance composite resin.

By inventing this new class of modified single-ring cyanate esters we have shown the ability to tailor and control the glass-transition (Tg) of the cured resins as well as the water uptake. Examples have been made that show a remarkably low water uptake and had no drop in the wet Tg as shown in Table 1. This is unusual and a very desirable property. In addition, the monomers can be made from sustainable and renewable bioaromatic feedstocks.

Data in Table 1 shows how by changing the ester group from propyl to ethylhexyl (EH) we dramatically lower the water uptake from 2.93 wt-% (propyl ester) down to 0.83 wt-% ER ester. This is a dramatic and unprecedented lowering in water uptake for a pure hydrocarbon based cyanate ester resin.

TABLE 1

Data for cured cyanate esters based on 3,5-bis(cyanate)benzaoate esters.
EH is used as an abbreviation for (2-ethylhexyl).

| Sample | CTE (ppm/° C.) | Dry Loss Peak (° C.) | Dry Tan Delta (° C.) | FC Loss Peak (° C.) | FC Tan Delta (° C.) | Wet Loss Peak (° C.) | Wet Tan Delta (° C.) | Cure Enthalpy (J/g) | Water Uptake (wt %) |
|---|---|---|---|---|---|---|---|---|---|
| EH Ester | 127 (50° C.) | 150 | 155 | 151 | 155 | 148 | 149 | 614 | 0.83 |
| Propyl Ester | 91 (150° C.) | 224 | 229 | 206 | 213 | 159 | 171 | 790 | 2.93 |

Figure 1:
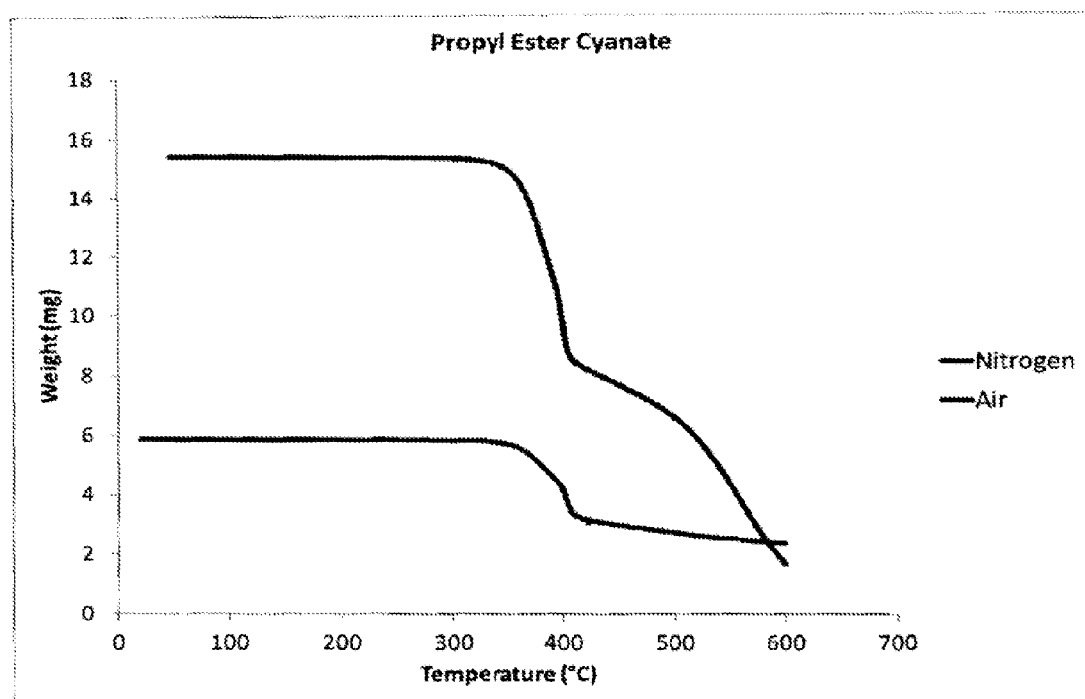
FIG. 1 is a graph showing thermogravimetric analysis (TGA) of propyl 35-bis(cyanato)benzoate under a nitrogen and air purge, according to embodiments of the invention.
Figure 2:
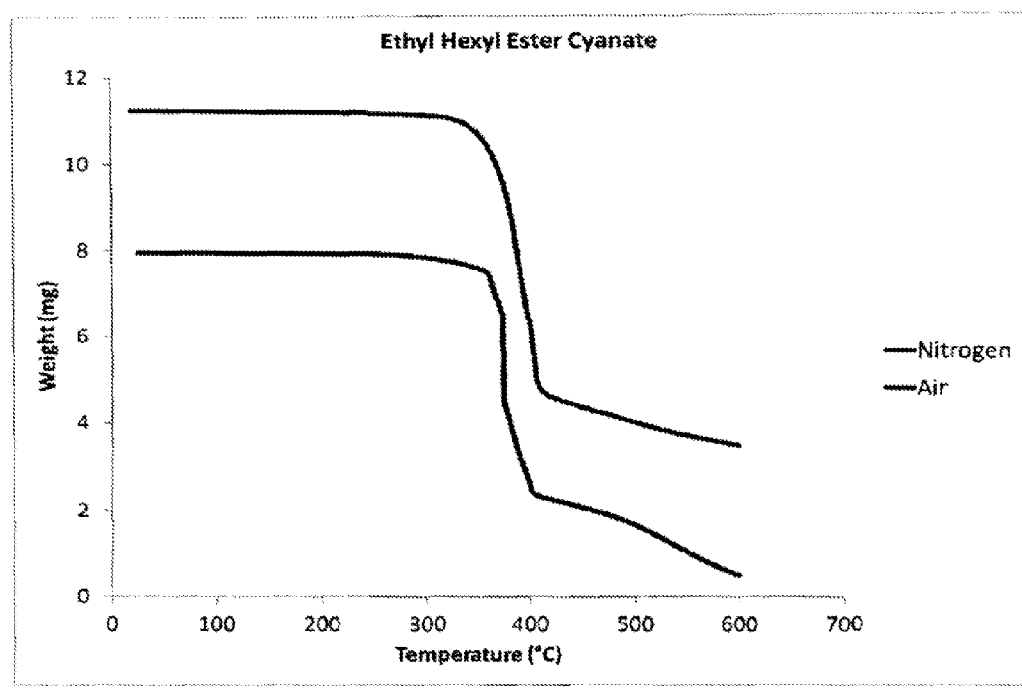
FIG. 2 is a graph showing thermogravimetric analysis (TGA) of ethylhexyl 3,5-bis(cyanato)benzoate under a nitrogen and air purge, according to embodiments of the invention.
Figure 3:
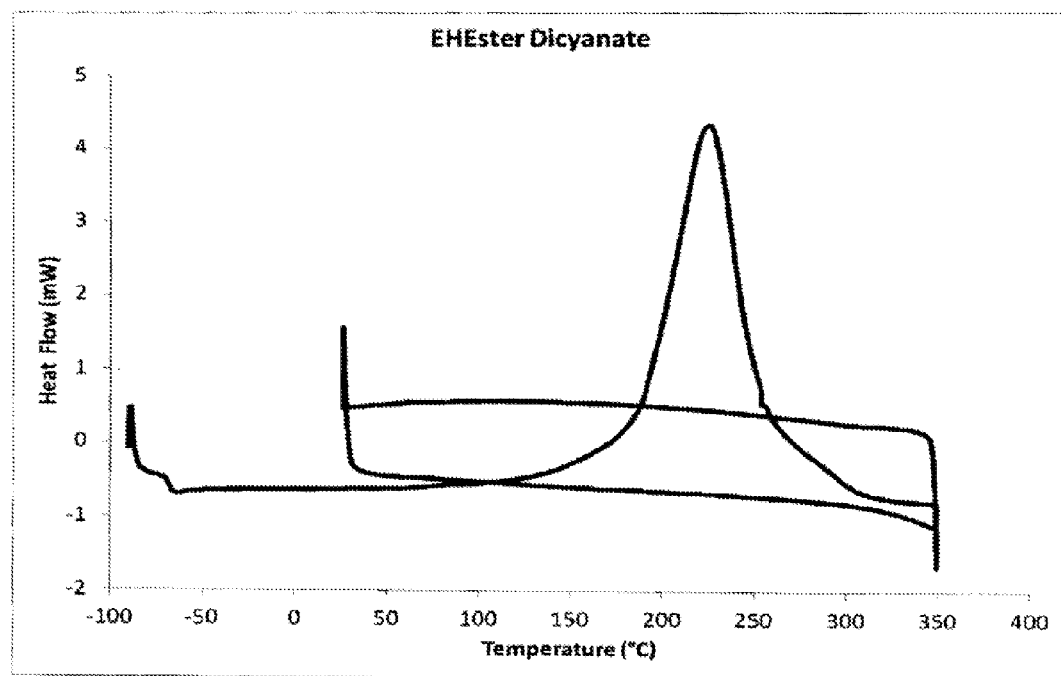
FIG. 3 is a graph showing Differential Scanning Calorimetry (DSC) analysis of ethylhexyl 3,5-bis(cyanato)benzoate under a nitrogen purge. Heating rate of 10° C./min, according to embodiments of the invention.
Figure 4:
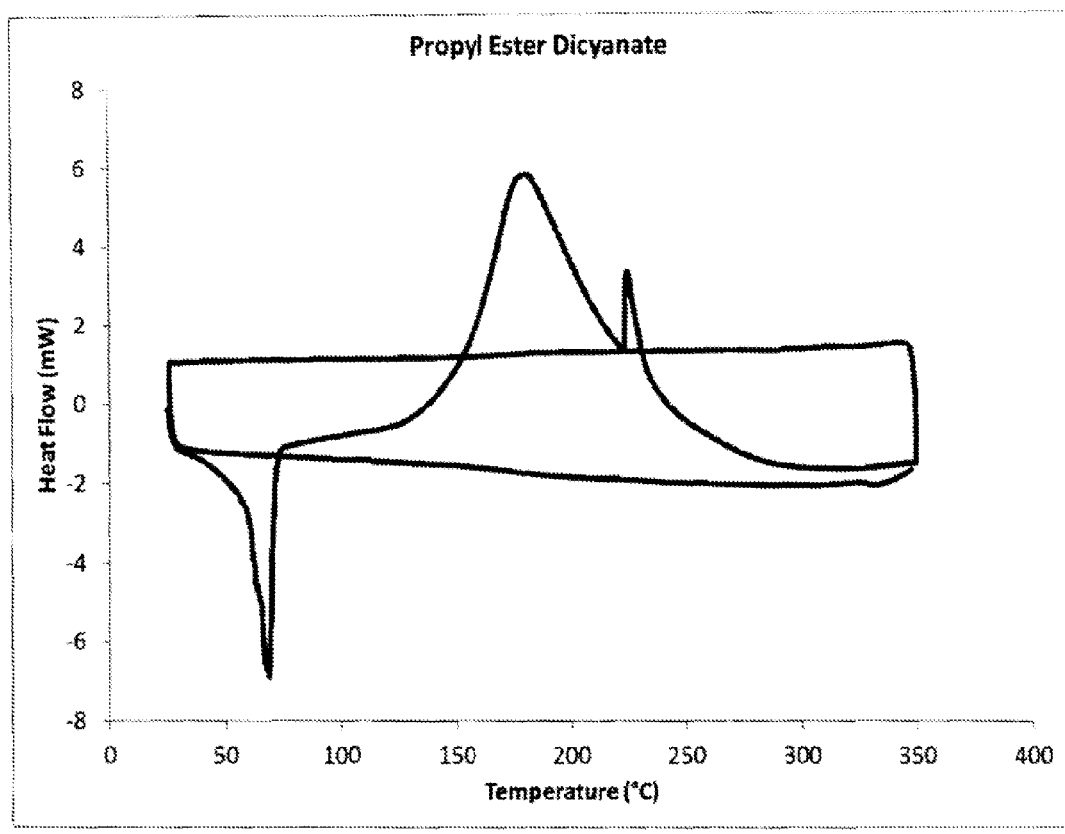
FIG. 4 is a graph showing Differential Scanning Calorimetry (DSC) analysis of propyl 3,5-bis(cyanato)benzoate under a nitrogen purge. Heating rate of 10° C./min according to embodiments of the invention.
Figure 5:
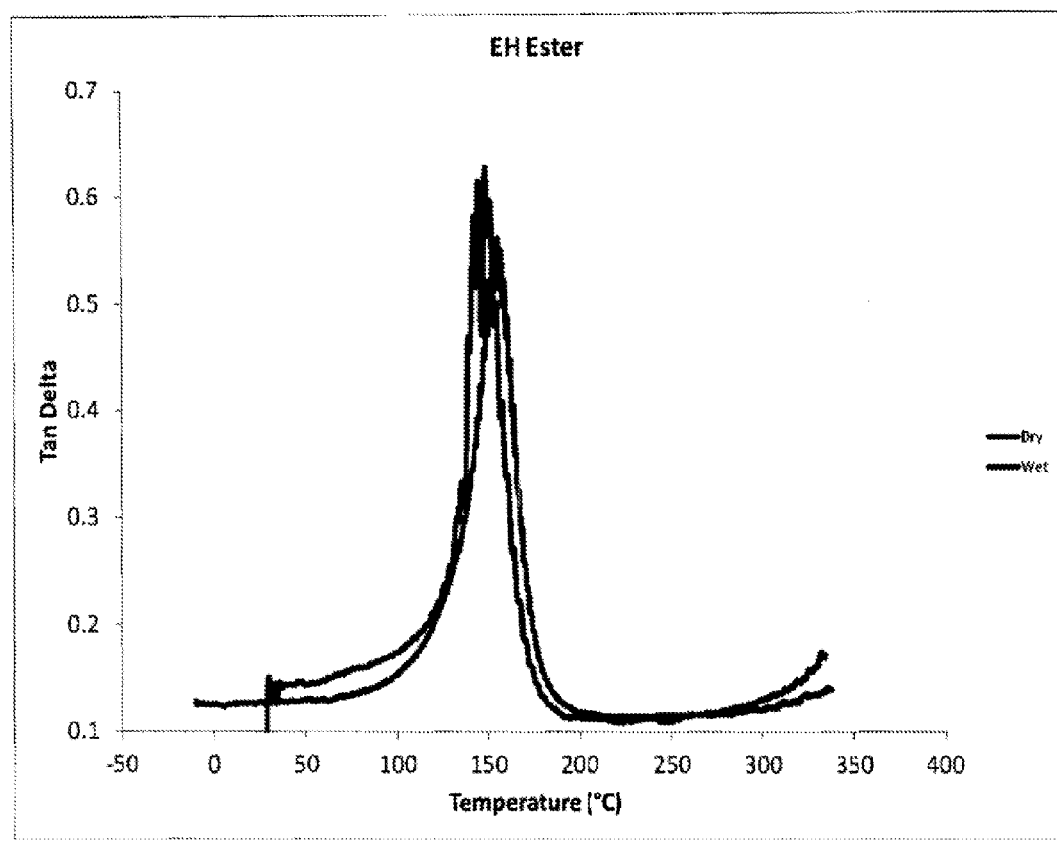
FIG. 5 is a graph showing thermomechanical analysis (TMA) analysis of ethylhexyl 3,5-bis(cyanato)benzoate under a nitrogen purge. Heating rate of 10° C./min, according to embodiments of the invention.

Further data to support the unexpected and desirable manner by which the physical properties of the bis(cyanate) monomer and that of the cured resins are shown in FIGS. 1-5. FIGS. 1 and 2 show that by having a larger alkyl group leads greater weight loss at high temperature, not an unexpected result. FIGS. 3 and 4 show each fully cure after one cycle in the DSC instrument. In FIG. 5 we see the unexpected result that we Tg for the cured resin is not affected by water. This is a truly astounding documented result for these novel resins.

Embodiments of the invention generally relate to methods for preparing 3,5-bis(cyanato)benzoate esters including, preparing a mixture 3,5-dihydroxybenzoic acid and at least one alcohol, heating the mixture in the presence of an acid catalyst, removing unreacted alcohol by distillation, purifying the 3,5-dihydroxybenzoate ester (I) from the mixture,

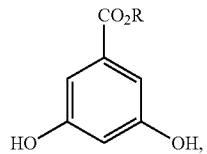
(I)

treating the ester (I) with cyanogen halide in the presence of at least one base and at least one solvent, isolating a 3,5-bis(cyanato)benzoate ester (II) from the treated ester (I),

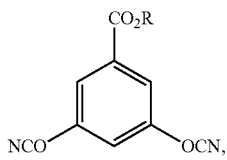
(II)

and purifying the 3,5-bis(cyanato)benzoate ester (II) to attain a cyanate ester monomer capable of forming thermally cured resins.

Other embodiments of the invention generally relate to methods for preparing 3,5-bis(cyanato)benzoate esters including, preparing a mixture 3,5-dihydroxybenzoic acid and at least one amine, heating the mixture in the presence of an acid catalyst, purifying said 3,5-dihydroxybenzamide (III) from the mixture,

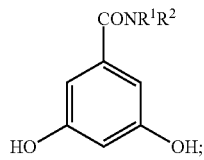
(III)

treating (III) with cyanogen halide in the presence of at least one base and one solvent, isolating the 3,5-bis(cyanato)benzamide (IV) from the treated (III),

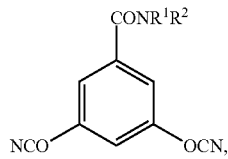
(IV)

and purifying the 3,5-bis(cyanato)benzamide (IV) to attain a cyanate ester monomer capable of forming thermally cured resins.

Embodiments of the invention generally relate to methods for preparing 3,5-bis(cyanato)benzoate esters including, reacting 3,5-di(benzyloxy)benzoic acid with oxalyl chloride, treating the acid/chloride with an alcohol in the presence of a base to form (V),

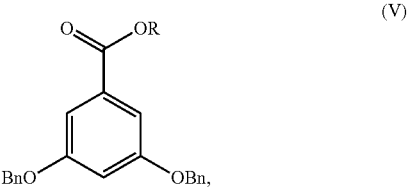
(V)

dissolving the (V) in at least one solvent, adding a solid catalyst and hydrogen gas, and reacting by stirring for about 2 to about 48 hours, removing of the catalyst by filtration and solvents by evaporation forming 3,5-dihydroxybenzoate ester (I), purifying, the 3,5-dihydroxybenzoate ester (I), treating the 3,5-dihydroxybenzoate ester (I) with cyanogen halide in the presence of at least one base and at least one solvent forming 3,5-bis(cyanato)benzoate ester (II), isolating the 3,5-bis(cyanato)benzoate ester (II), and purifying the 3,5-bis(cyanato)benzoate ester (II) to attain a cyanate ester monomer capable of forming thermally cured resins.

In embodiments, the alcohol is an aliphatic alcohol having 1 to about 24 carbons. In other embodiments, the alcohol is an aliphatic alcohol having 1 to about 24 carbons and including at least one fluorine atom. In yet other embodiments, the alcohol is both aliphatic and aromatic in composition having a total of about 5 to about 24 carbons. In embodiments, the aromatic includes at least one fluorine atom and a total of about 5 to about 24 carbons. In embodiments, the halide is selected from the group consisting of bromide, chloride, and iodide. In embodiments, the amine is an aliphatic amine having 1 to about 30 carbons. In embodiments, the amine is an aliphatic amine having 1 to about 30 carbons and includes at least one fluorine atom. In embodiments, the amine is both aliphatic and aromatic in composition having a total of about 5 to 30 about carbons. In embodiments, the aromatic includes at least one fluorine atom and a total of about 5 to about 30 carbons.

In embodiments, said halide is selected from the group consisting of bromide, chloride, and iodide. Embodiments further include thermal curing of said 3,5-bis(cyanato)benzoate esters (II) to form composite parts with low water uptake. Embodiments further include thermal curing of said 3,5-bis(cyanato)benzamides (IV) to form composite parts with low water uptake. Embodiments further include thermal curing of a mixture of said 3,5-bis(cyanato)benzoate esters (II) and 3,5-bis(cyanato)benzamides (IV) to form composite parts with low water uptake where (II) can be from 1 to 99% of the mixture. In embodiments, the base is selected from an aliphatic amine including from about 3 to about 18 carbons. In embodiments, the base is an amine supported on crosslinked polymeric support. In embodiments, the oxalyl chloride is used as 1.0 to 1.5 mol-equivalent to the 3,5-di(benzyloxy)benzoic acid. In embodiments, the hydrogenation catalyst uses at least one metal selected from palladium and platinum. In embodiments, the palladium is supported on a carbon, in embodiments, the platinum oxide is the catalyst used in 0.01 to 2 wt-% of said 3.5-di(benzyloxy)benzoate ester (V).

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for preparing 3,5-bis(cyanato)benzoate esters, comprising:
   preparing a mixture 3,5-dihydroxybenzoic acid and at least one aliphatic and/or aromatic alcohol (ROH), wherein R is an aliphatic and/or aromatic component of said aliphatic and/or aromatic alcohol;
   heating said mixture in the presence of an acid catalyst;
   removing unreacted alcohol by distillation;
   purifying said 3,5-dihydroxybenzoate ester (I) from said mixture:

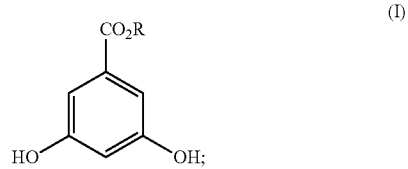

(I)

treating said ester (I) with cyanogen halide in the presence of at least one base and at least one solvent;
   isolating a 3,5-bis(cyanato)benzoate ester (II) from said treated ester (I):

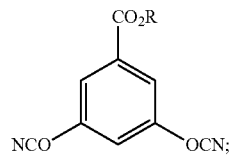

(II)

and
   purifying said 3,5-bis(cyanato)benzoate ester (II) to attain a cyanate ester monomer capable of forming thermally cured resins.

2. The method according to claim 1, wherein said alcohol is an aliphatic alcohol having 1 to about 24 carbons.

3. The method according to claim 1, wherein said alcohol is an aliphatic alcohol having 1 to about 24 carbons and including at least one fluorine atom.

4. The method according to claim 1, wherein said alcohol is both aliphatic and aromatic in composition having a total of about 5 to about 24 carbons.

5. The method according to claim 4, wherein said aromatic includes at least one fluorine atom and a total of about 5 to about 24 carbons.

6. The method according to claim 1, wherein said halide is selected from the group consisting of bromide, chloride, and iodide.

7. The method according to claim 1, further comprising thermal curing of said 3,5-bis(cyanato)benzoate esters (II) to form composite parts with low water uptake.

8. The method according to claim 1, further comprising thermal curing of said 3,5-bis(cyanato)benzamides (IV) to form composite parts with low water uptake.

9. The method according to claim 1, further comprising thermal curing of a mixture of said 3,5-bis(cyanato)benzoate esters (II) and 3,5-bis(cyanato)benzamides (IV) to form composite parts with low water uptake where (II) can be from 1 to 99% of the mixture.

* * * * *